(12) United States Patent
Fellows et al.

(10) Patent No.: US 6,659,301 B2
(45) Date of Patent: Dec. 9, 2003

(54) LIQUID VAPORIZATION DEVICE AND BOTTLE

(75) Inventors: Robert Terrence Fellows, Park Ridge, NJ (US); Alfred G. Prior, Upper Saddle River, NJ (US); Manfred Alois Riegg, Ringwood, NJ (US); Jeffrey Lawrence Stern, Rancho Santa Margarita, CA (US)

(73) Assignee: Waldwick Plastics Inc., Waldwick, NJ (US)

( * ) Notice: Subject to any disclaimer, the term of this patent is extended or adjusted under 35 U.S.C. 154(b) by 0 days.

(21) Appl. No.: 10/118,176

(22) Filed: Apr. 8, 2002

(65) Prior Publication Data

US 2003/0189022 A1 Oct. 9, 2003

(51) Int. Cl.[7] .......................... A61M 16/00; B65D 23/00; F24F 6/08
(52) U.S. Cl. ......................... 215/400; 215/40; 215/382; 215/395; 392/390; 392/395
(58) Field of Search ............................ 215/40, 43, 379, 215/382, 386, 395, 10, 400; 392/395, 390, 392–394; 122/366; 239/44; 261/DIG. 65

(56) References Cited

U.S. PATENT DOCUMENTS

| | | | | |
|---|---|---|---|---|
| 1,625,728 A | * | 4/1927 | Klein ........................ 215/382 |
| 2,424,045 A | * | 7/1947 | Millstein ................ 215/382 X |
| 3,362,530 A | * | 1/1968 | Johnson .................... 215/40 X |
| 4,391,781 A | | 7/1983 | van Lit |
| 4,467,177 A | | 8/1984 | Zobele |
| 4,725,712 A | | 2/1988 | Schroeder et al. |
| 4,731,520 A | | 3/1988 | Glucksman et al. |
| 4,734,560 A | | 3/1988 | Bowen |
| 4,739,928 A | * | 4/1988 | O'Neil ........................ 239/48 |
| 4,795,883 A | | 1/1989 | Glucksman et al. |
| 4,804,821 A | | 2/1989 | Glucksman |
| 4,816,973 A | | 3/1989 | Atalla et al. |
| 4,837,421 A | | 6/1989 | Luthy |
| 4,849,606 A | | 7/1989 | Martens, III et al. |
| 4,881,648 A | * | 11/1989 | Hagerty ................ 215/382 X |
| 4,968,487 A | * | 11/1990 | Yamamoto et al. ......... 422/125 |
| 5,014,913 A | * | 5/1991 | Hoyt et al. ................... 239/45 |
| 5,038,394 A | | 8/1991 | Hasegawa et al. |
| 5,095,647 A | * | 3/1992 | Zobele et al. ................. 43/125 |
| 5,111,477 A | | 5/1992 | Muderlak |
| 5,136,684 A | | 8/1992 | Lonker et al. |
| 5,175,791 A | | 12/1992 | Muderlak et al. |

(List continued on next page.)

FOREIGN PATENT DOCUMENTS

| | | |
|---|---|---|
| WO | WO 00/42839 | 7/2000 |
| WO | WO 00/48922 | 8/2000 |
| WO | WO 00/69479 | 11/2000 |
| WO | WO 01/21226 | 3/2001 |

*Primary Examiner*—Sue A. Weaver
(74) *Attorney, Agent, or Firm*—Gibbons, Del Deo, Dolan, Griffinger & Vecchione

(57) ABSTRACT

A universal bottle that interfits into a plurality of different housings for liquid vaporization devices. Two of the current commercial devices have specially constructed bottles that are not interchangeable, that is, the bottle intended for use with one of the commercial devices cannot be used with the other device and vice versa. The present bottle is dimensioned so as to interfit into both of the commercial devices and has a neck having an opening and two sets of opposite external surfaces that are dimensioned so that in one orientation, the bottle will fit into one of the commercial devices, and, by rotating the bottle a predetermined amount to another orientation, the bottle can be operatively inserted into the other of the commercial devices. In each instance, a locking system on the bottle cooperates with the housing of the commercial device to retain the bottle in its operative position.

22 Claims, 3 Drawing Sheets

U.S. PATENT DOCUMENTS

| | | |
|---|---|---|
| 5,201,025 A | 4/1993 | Landesberg |
| 5,213,523 A | 5/1993 | Hygema et al. |
| 5,220,636 A | 6/1993 | Chang |
| 5,222,186 A * | 6/1993 | Schimanski et al. ........ 392/395 |
| 5,271,560 A * | 12/1993 | De Winter ................... 239/42 |
| 5,354,540 A | 10/1994 | Neumiller |
| 5,402,517 A | 3/1995 | Gillett et al. |
| 5,521,357 A | 5/1996 | Lock et al. |
| 5,522,008 A | 5/1996 | Bernard |
| 5,556,192 A | 9/1996 | Wang |
| 5,557,156 A | 9/1996 | Elings |
| 5,574,821 A | 11/1996 | Babasade |
| 5,647,052 A | 7/1997 | Patel et al. |
| 5,647,053 A | 7/1997 | Schroeder et al. |
| 5,796,914 A | 8/1998 | Gatzemeyer et al. |
| 5,903,710 A | 5/1999 | Wefler et al. |
| 5,909,845 A | 6/1999 | Greatbatch et al. |
| 5,926,614 A | 7/1999 | Steinel |
| 5,937,140 A | 8/1999 | Leonard et al. |
| 5,940,577 A | 8/1999 | Steinel |
| 5,945,094 A | 8/1999 | Martin et al. |
| 5,976,503 A | 11/1999 | Martin et al. |
| 6,031,967 A | 2/2000 | Flashinski et al. |
| 6,044,202 A | 3/2000 | Junkel |
| 6,078,728 A | 6/2000 | O'Rourke et al. |
| 6,085,026 A | 7/2000 | Hammons et al. |
| 6,097,881 A | 8/2000 | DeWitt et al. |
| 6,101,315 A | 8/2000 | Steinel, Jr. |
| 6,104,866 A | 8/2000 | DeWitt et al. |
| 6,104,867 A | 8/2000 | Stathakis et al. |
| 6,123,935 A | 9/2000 | Wefler et al. |
| 6,141,496 A | 10/2000 | Sundberg et al. |
| 6,148,143 A | 11/2000 | Steinel, Jr. |
| 6,154,607 A | 11/2000 | Flashinski et al. |
| D439,319 S * | 3/2001 | Wolpert ..................... D23/363 |
| 6,236,807 B1 | 5/2001 | Ruffolo et al. |
| 6,278,840 B1 | 8/2001 | Basaganas Millian |
| 6,285,830 B1 | 9/2001 | Basaganas Millan |
| 6,289,176 B1 | 9/2001 | Martter et al. |
| 6,318,876 B1 | 11/2001 | Sigro et al. |
| 6,466,739 B2 * | 10/2002 | Ambrosi et al. ............ 392/395 |
| 2001/0053283 A1 | 12/2001 | Levine et al. |
| 2002/0172512 A1 * | 11/2002 | Stathakis et al. |

\* cited by examiner

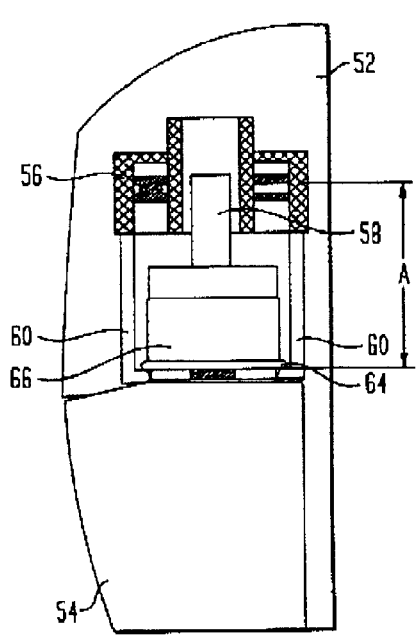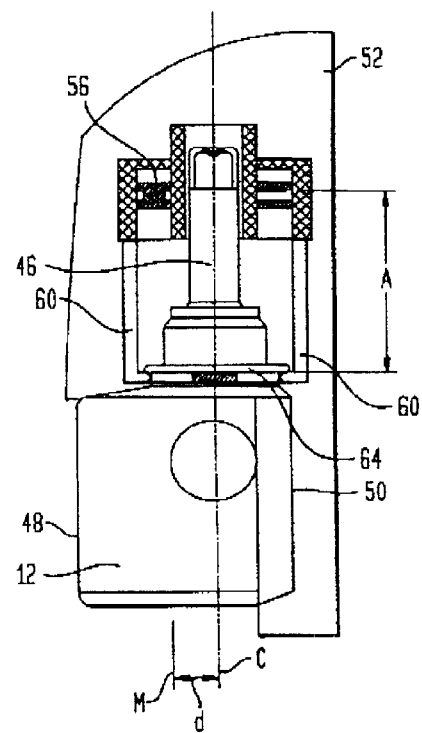

LIQUID VAPORIZATION DEVICE AND BOTTLE

BACKGROUND

The present invention relates to liquid vaporization devices and, more particularly, to a device that vaporizes a liquid perfume and to a specialized bottle that can be used therewith.

There are, of course, a number of commercial devices currently on the market that are capable of vaporizing an aroma producing liquid in order to freshen a room and to rid that room of annoying and undesirable odors. Of the typical commercial devices, there is the type that includes a housing that receives a liquid containing bottle such that the user can employ the device to vaporize the liquid within the bottle and, when the supply of liquid within a particular bottle has been expended, the user can simply remove the empty bottle and replace it with a full bottle to continue the utilization of the device. As such, the typical device comprises a housing having a heater contained therein and which interacts with a wick extending upwardly from the bottle.

The heater, therefore, must be in close proximity to the wick when the bottle is interfitted to the housing so that the heater for that device can effectively and efficiently vaporize the liquid that is present in the wick. In some vaporizing devices, the heater is an annular unit that surrounds the wick and therefore it is critical, in such devices, that the wick be properly positioned with respect to the heater and be capable of easily and automatically be located in such position when a bottle is inserted in to the vaporization device. The heater warms the wick, thereby enhancing the vaporization process, and which also draws that liquid upwardly from that bottle. The bottle itself therefore requires an opening at the top surface such that the wick can extend upwardly through that opening and into the housing of the particular vaporization device so that the wick is properly aligned with the heater.

One of the drawbacks to current liquid vaporization devices, however is that each bottle is unique to a particular housing, that is, once the consumer has purchased a liquid vaporization device, there is a limited market to the purchase of replacement bottles and only a certain bottle will interact with a housing of any individual manufacturer. For example, two of the popular commercial liquid vaporization devices currently on the market are the Wizard device distributed by Reckitt Benckiser, Inc, of Wayne, N.J. and the Glade device manufactured by S.C. Johnson and Son of Wisconsin. Each device has different dimensions of its housing that accepts a bottle filled with liquid perfume and each bottle is differently dimensioned such that the bottle presently sold to be used with the Glade device cannot be used with the Wizard device and vice versa.

Not only are there dimensional differences, but with the Wizard device, the bottle has an annular collar that is snap fitted to a movable member to retain the bottle in its operative position to the housing and there is a release mechanism that moves that movable member to release the bottle therefrom. As such, with the bottle adapted to be interfitted to the Wizard device, there needs to be a annular collar that is dimensioned so as to properly cooperate with the snap in and release mechanism. In addition, with the Wizard unit, as with other bottles, and as explained, the location of the opening in the bottle through which the wick extends, is important and in the Wizard device that bottle opening is off center, that is, it is not centered between the front and rear surfaces of the bottle as it is positioned within the housing of the Wizard device. As used herein, the rear surface of a bottle is the surface that faces the vaporization device and the front surface faces outwardly away from that device.

Accordingly, with the Wizard device, taking a dimension of the bottle along a centerline or plane extending at a right angle to the rear surface of the housing such that the centerline passes through the front surface of the bottle and the rear surface of the bottle, the opening for the wick, and, of course, the wick itself, is located closer to the rear surface than the front surface.

With the Glade device, the location of the opening in the upper surface of the bottle is in an entirely. different position with respect to its front and rear surfaces and, again, such location is essential to the proper interfitting of the bottle into the housing of the Glade device. Thus, in the Glade device, the location of its opening, and, of course, the corresponding wick that extends upwardly from the opening, is positioned approximately centered between its front and rear surfaces. With the bottle used in the Glade device, the bottle also has two oppositely disposed projections that interfit into corresponding shaped openings in the housing so that the projections snap into the openings in the housing to retain the bottle in its operative position and the bottle can be snapped out of that position by the inherent flexibility of the housing. Those projections are, therefore, formed in the front and rear surfaces of the bottle for the Glade device, and, therefore, generally at equal distances from the centerline of the opening in the upper surface of the Glade bottle.

As can be seen, the differences in the current bottles for the Glade and Wizard devices, be it based upon the dimensions of the external surfaces or in the location of the opening for the wick, makes the bottles that interfit into those devices unique to each intended device and the interchangeability not possible, that is, a bottle intended for a Glade device simply cannot be used with a Wizard device and vice versa.

Accordingly, the consumer cannot have the versatility of having a differing brand of vaporization devices without having to make sure the proper bottle is purchased for that specific vaporization device and it is possible for the consumer to actually purchase the incorrect bottle and thus be thwarted in the desire to replace an existing, empty bottle. In addition, the consumer is sometimes inconvenienced in that a local store may stock only one brand of liquid vaporization device and which is not compatible with the device that is being used by the consumer, thereby requiring the consumer to locate another supplier of the correct bottle.

In addition, aside from the lack of versatility in purchasing bottles that are specific to a particular vaporization device, it is more convenient for the consumer to have the ability to purchase a range of scents, and a particular desired scent may be available only from a competing manufacturer of the consumers devices and therefore the consumer cannot use that particular scent due to the incompatibility of the bottle containing that scent with the device in use by the consumer.

In any event, it would be advantageous for the consumer to be able to purchase a single bottle that is compatible physically with more than one brand of liquid vaporization device so that such consumer can simply purchase the bottle having the desired scent and be able to use that bottle irrespective of the brand of the liquid vaporization device used by the consumer.

SUMMARY OF THE INVENTION

Accordingly, the present invention relates to a liquid vaporization device and bottle that interfits therewith and to a specially constructed bottle that can fit into any of a plurality of housings of such vaporization devices and, at least into those housings of the Glade and the Wizard liquid vaporization devices.

Accordingly the bottle of the present invention has solved the lack of interchangeability of the aforementioned bottles for the commercial Glade and Wizard liquid vaporization devices by providing a neck having an opening along with a plurality of front and rear external surfaces that are selectable by the user, that is, the bottle is capable of being utilized in a multiplicity of orientations with respect to the particular housing of a liquid vaporization device.

The bottle of this invention can be oriented in one position wherein the opening is centrally located between the front and rear surfaces of the bottle as it is interfitted to the Glade liquid vaporization device with the front and rear surfaces additionally having projections extending out therefrom to snap within corresponding alignment holes in the Glade housing for that device. Thus, in such orientation, the bottle is well adapted to be interfitted to the Glade device.

By rotating the present bottle a predetermined amount, or number of degrees, a different front and rear surface is presented and where the upwardly facing opening is now closer to the rear surface than the front surface, i.e. offset from the center location between the front and rear surfaces, and is therefore adapted to be interfitted to the housing of the Wizard liquid vaporization device. There is additionally formed an annular collar so that the bottle, in this orientation, can be interfitted to and held in the housing of a Wizard device.

Thus, by simply rotating the bottle, two different sets of front and rear surfaces are utilized, each having the proper characteristics, dimensions and features necessary for the proper fitting of the bottle into either the Glade of the Wizard device and with the opening located in the proper positioned to operate with that particular device. With each orientation, the bottle includes a locking feature that cooperates with a corresponding feature on the Glade or Wizard device housing to retain the bottle in its operative position. In the preferred embodiment, that amount of rotation used to orient the bottle with the differing front and rear surfaces to carry out the present invention is 90 degrees.

Additional features and advantages of the invention will become apparent to those skilled in the art upon consideration of the following detailed description of preferred embodiments exemplifying the best mode of carrying out the invention.

BRIEF DESCRIPTION OF THE DRAWINGS

FIG. 5A is a side view of a prior art liquid vaporization housing utilizing a prior art bottle; and FIG. 5B is a side view of the prior art liquid vaporization housing of FIG. 5A utilizing a bottle constructed in accordance with the present invention.

DETAILED DESCRIPTION OF THE INVENTION

Figure 1:
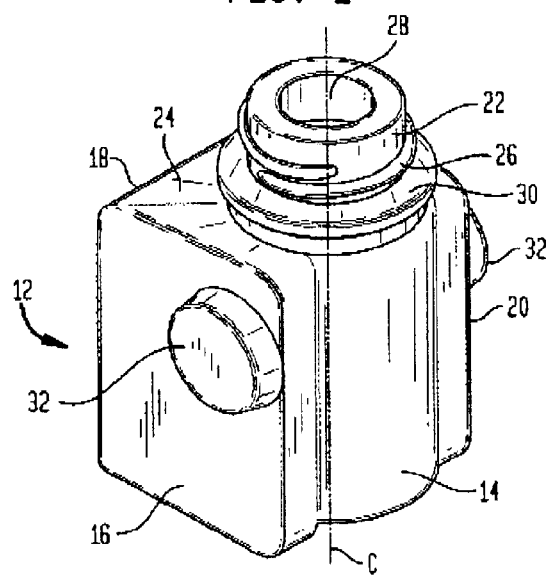
FIG. 1 is perspective view of a bottle for use with a liquid vaporization device constructed in accordance with the present invention and having first, second, third and fourth external surfaces.

Referring now to FIG. 1, there is shown a perspective view of a bottle 12 constructed in accordance with the present invention. In FIG. 1, it can be seen that there are basically four external surfaces to the bottle 12. For purposes explaining the present invention the external surfaces are defined in FIGS. 1–3 as a first external surface 14, a second external surface 16, a third external surface 18 and a fourth external surface 20. The first external surface 14 is preferably arcuate in configuration, that is, it is curved outwardly, while the surfaces of second, third and fourth external surfaces 16, 18, and 20, respectively, are generally planar, however, it will become apparent that any of the external surfaces may be arcuate or planar and still be within the spirit of the present invention. As an example, in the preferred embodiment, the width of the first and third external surfaces 14, 18 is about 32.3 mm. while the width of the second and fourth external surfaces 16 and 20 is about 35.6 mm.

A neck 22 extends upwardly for the upper surface 24 of the bottle 12 and the neck 22 is preferably provided with external threads 26 so that a protective cap (not shown) may readily be secured to the bottle 12 to contain the contents of the bottle 12 prior to use. In the preferred embodiment, the overall height of the bottle 12 from the bottom of the bottle 12 to the top of the neck 22 is about 52 mm. There is an opening 28 that passes through the neck 22 to communicate with the interior of the bottle 12, and, as will be later explained, a wick is adapted to extend upwardly through the opening 28 so that a liquid contained within the bottle 12 can pass through the wick to be vaporized to the atmosphere.

There is also formed integral with the neck 22 an annular collar 30 that is dimensioned to be a predetermined diameter and location on the bottle 12 for purposes that will also be later explained. There are also a pair of outwardly extending projections 32 that are formed in the second and fourth external surfaces 16, 20 and are oriented opposite each other and generally in alignment with the opening 28 in the neck 22, that is, the longitudinal center line C of the opening 28 and the center line joining the projections 32 would be in the same plane.

Figure 2:
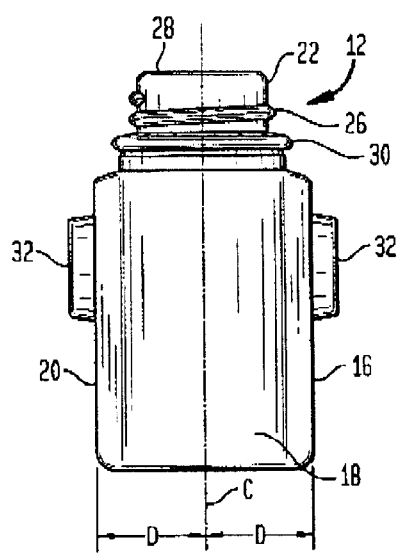
FIG. 2 is a side view of the bottle of FIG. 1 facing the third surface thereof.

Taking FIG. 2 in connection with FIG. 1, it can be seen that the center line C of the opening 28 is also oriented about midway between the second and fourth external surfaces 16, 20, show by the distances D in FIG. 2.

Figure 3:
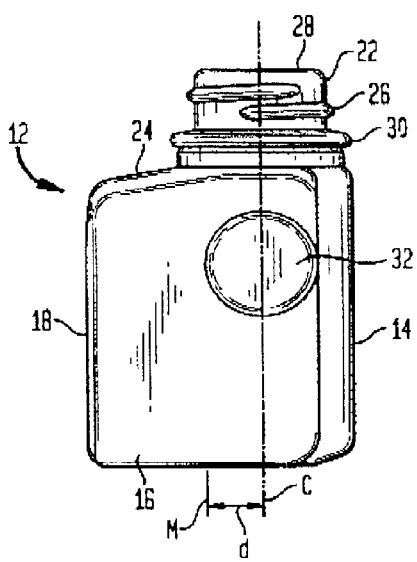
FIG. 3 is a side view of the bottle of FIG. 1 facing the second surface thereof.

Turning now to FIG. 3 in connection with FIG. 1, it can also be seen that the centerline C of the opening 28 is offset with respect to the midpoint between the first and third external surfaces 14 and 18. For example in FIG. 3, the mid point between the first and the second external surfaces 14 and 18 is shown as point M and the centerline of the opening 28 is offset with respect to that mid point M by a predetermined dimension d. FIG. 3 also shows the alignment between the centerline of the projections 32 and the centerline C of the opening 28. In the preferred embodiment, the approximate distance from the second external surface 18 to the centerline C is about 23.1 mm and from that centerline C to the first external surface 14 is about 12.5 mm.

Figure 4A:
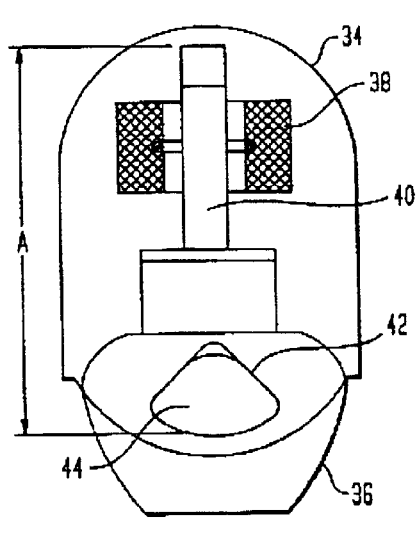
FIG. 4A is a front view of a prior art liquid vaporization housing utilizing a prior art bottle.
Figure 4B:
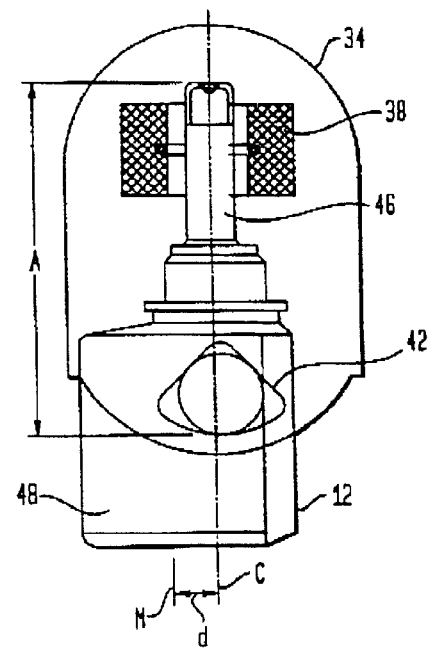
FIG. 4B is a front view of the prior art liquid vaporization housing of FIG. 4A utilizing a bottle constructed in accordance with the present invention.

Turning now to FIGS. 4A and 4B, there is shown front views of a commercial liquid vaporization device having a housing 34 that is basically typical of the Glade device that is currently on the market. In FIG. 4A, there is a standard prior art bottle 36 currently sold with or sold to be used with the Glade device and is affixed in its operative position to the housing 34 and in FIG. 4B, there is affixed to the housing 34 the bottle 12 constructed in accordance with the present invention.

Taking FIG. 4A first, it can be seen that the housing 34 includes a annular heater 38 that surrounds the wick 40 extending upwardly from the bottle 36. Thus, when the bottle 36 is in its operative position, as shown, the wick 40 passes through the annular heater 38 so that the heater 38 can heat the volatile liquid within the wick 40 and vaporize that liquid to be exhausted into the surrounding environment.

The housing 34 also includes two alignment holes 42 (only one of which is shown in FIG. 4A) that are oppositely oriented such that two projections 44 on the bottle 36 can be snapped into the alignment holes 42 as the bottle 36 is inserted into its operative position within the housing 34 to hold the bottle 36 in that operative position and, by predetermining the dimension A, it is assured that the wick 40 is sufficiently long so as to pass sufficiently through the annular heater 38 when the lower edge of the projections 44 are snap fitted into the corresponding alignment holes 42.

Thus, in FIG. 4B, the same housing is used as representative of the Glade liquid vaporization device and therefore the dimension A is still important to assure that the wick 46 of the bottle of this invention is sufficiently long to pass within the annular heater 38. Also of critical dimension, and referring also back to FIGS. 1 and 3, in FIG. 3 the bottle 12 is shown in the same orientation as in the front view of FIG. 4B such that the wick 46 extending from the opening 28 is located at the midpoint between the front external surface 48 and the rear external surface (not shown in FIG. 4B). To put the orientation in perspective, and referring to FIGS. 1–3 and 4B, the front external surface 48 is the external surface that faces away from the housing 34 and is, in effect, the second external surface 16 of FIGS. 1–3 and the rear surface of FIG. 4B, not shown in FIG. 4B, that is, the external surface facing the housing 34 is the fourth external surface 20 of FIGS. 1–3. As can also be seen, the bottle 12 can be rotated 180 degrees and still interfit within the housing 34, that is, the bottle 12 would be a mirror image of the bottle 12 shown in the orientation of FIG. 4B.

Therefore, in order to fit within the housing 34 of the Glade liquid vaporization device, the bottle 12 must be orientated such that the second external surface 16 or the fourth external surface 20 of FIGS. 1–3 is the front surface 48 of FIG. 4B and the fourth external surface 20 or the second external surface 16 of FIGS. 1–3 is the rear external surface of the bottle of FIG. 4B, that is, the bottle 12 can be placed in the Glade device in either of two positions that are 180 degrees apart.

Turning now to FIGS. 5A and 5B, there is shown side views of a commercial liquid vaporization device having a housing 52 that is basically typical of the Wizard device that is currently on the market. In FIG. 5A, there is a standard prior art bottle 54 currently sold to be used with the Wizard device and is affixed in its operative position to the housing 52 and in FIG. 5B, there is affixed to the housing 52 the bottle 12 constructed in accordance with the present invention.

Taking FIG. 5A first, it can be seen that the housing 52 includes an annular heater 56 that surrounds the wick 58 extending upwardly from the bottle 54. Thus, when the bottle 54 is in its operative position, as shown, the wick 58 passes through the annular heater 56 so that the heater can heat the volatile liquid within the wick 58 and vaporize that liquid to be exhausted into the surrounding environment.

The housing 52 also includes downwardly extending latches 60 that grasps the bottle 54 underneath the annular collar 64 formed in the neck 66 of the bottle 54. The interaction between the downwardly extending latches 60 thus holds the bottle 54 in its operative position as show in FIG. 5A. Again, by predetermining the dimension A, it is assured that the wick 58 is sufficiently long so as to assure that the wick 58 passes through the annular heater 56 when the downwardly extending latches 60 have securely grasped and are holding the bottle 54 in the operative position as shown in FIG. 5A.

Thus, in FIG. 5B, the same housing is used as representative of the Wizard liquid vaporization device and therefore the dimension A is still important to assure that the wick 46 of the bottle of this invention is sufficiently long to pass within the annular heater 56. Also of critical dimension, and referring also back to FIGS. 1 and 2, in FIG. 3 the bottle 12 is shown in the same orientation as in the side view of FIG. 5B such that the wick 46 extending from the opening 28 is located offset rearwardly in the housing 52 from the point M that is the midpoint between the front external surface 48 and the rear external surface 50. To put the orientation in perspective, and referring to FIGS. 1–3 and 5B, the front external surface 48 is the external surface that faces away from the housing 52 and is, in effect the third external surface 18 of FIGS. 1–3 and the rear external surface 50 of FIG. 4B, i.e. the external surface facing the housing 52, is the first external surface 14 of FIGS. 1–3.

Therefore, in order to fit within the housing 52 of the Wizard liquid vaporization device, the bottle 12 must be orientated such that the third external surface 18 of FIGS. 1–3 is the front surface 48 of FIG. 5B and the first external surface 14 of FIG. 1–3 is the rear external surface 50 of the bottle 12 of FIG. 5B.

Therefore, it can be seen that the present bottle 12 can be interfitted into the Glade vaporization device or the Wizard vaporization device by simply rotating the bottle 12 so that the proper external surfaces are in the correct orientation with respect to the particular commercial device, be it the Glade device or the Wizard device.

To summarize, with the present bottle 12, it is possible to interfit that bottle 12 into either the housing 34 of the Glade device as shown in FIGS. 4A and 4B or the Wizard device as shown in FIGS. 5A and 5B by simply rotating the bottle about its centerline C passing through the opening 28 and the neck 22 so that different external surfaces are facing toward and away from the housing 34 and 52. For example, when the bottle 12 is intended to be interfit into the housing 34 of the Glade device, the bottle is oriented such that the second and fourth external surfaces 16 and 20 as shown in FIGS. 1–3 are, respectively, the front and rear surfaces of the bottle 12 when operatively interfitted with that Glade device and shown in FIG. 4B. On the other hand, to interfit the same bottle 12 into the Wizard device, the bottle 12 is simply rotated 90 degrees and inserted into the Wizard device such that the first external surface 14 and the third external surface 18 of FIGS. 1–3 are, respectively, the rear surface 50 and the front surface 48 of the bottle 12 when in the operative position in that Glade device, shown in FIG. 5B.

Accordingly, the present bottle 12 has been specifically dimensioned to be able to be interfitted with either the Glade device or the Wizard device through the rotation of the bottle 12 such that the proper dimensions are in the correct location to insert that bottle 12 into either device and thus the same bottle can be sold commercially at a greater convenience to the user. It should be noted, that the present bottle can only be interfitted to the Wizard unit in one orientation and can thereafter be interfitted to the Glade device by a 90 degree rotation of the bottle 12 in either direction, that is, the bottle 12 can fit into the Glade device in two orientations, about 180 degrees apart, with either the second external surface 16 or the fourth external surface 20 facing outwardly.

Those skilled in the art will readily recognize numerous adaptations and modifications which can be made to the liquid vaporization device and bottle which will result in an improved device and method of using the same yet all of which will fall within the scope and spirit of the present invention as defined in the following claims. Accordingly, the invention is to be limited only by the following claims and their equivalents.

We claim:

1. A liquid vaporization device having a bottle removably affixed thereto, said bottle having a neck forming an opening extending upwardly therefrom, said bottle having a first set of opposed exterior surfaces and a second set of opposed exterior surfaces, said opening being located approximately at the midpoint between said first set of opposed exterior surfaces, said opening being located displaced a predetermined distance away from the midpoint between said second set of exterior surfaces, the bottle having an annular collar surrounding the opening and at least one projection extending outwardly from one of the sets of opposed surfaces, the bottle being affixable to the liquid vaporization device by means of either, but not necessarily both, the annular collar or the at least one projection.

2. The liquid vaporization device as defined in claim 1 wherein said first set of opposed exterior surfaces of the bottle includes at least one projection extending outwardly from each of said opposed surfaces.

3. The liquid vaporization device as defined in claim 2 wherein said projections are aligned with said opening in said bottle.

4. The liquid vaporization device as defined in claim 1 wherein at least one of said second set of opposed exterior surfaces is an arcuate surface.

5. The liquid vaporization device as defined in claim 1 wherein said first and said second set of opposed exterior surfaces is angularly displaced from each other at a predetermined angle about the bottle.

6. The liquid vaporization device as defined in claim 5 wherein said predetermined angle is about 90 degrees.

7. A liquid vaporization device having a bottle removably affixed thereto, said liquid vaporization device having one of a receiving structure or a releasable securing means, a bottle having an outlet opening and adapted to interfit within the liquid vaporization device, the bottle having a projection extending outwardly therefrom and an annular collar surrounding the outlet opening, the bottle being affixable to the liquid vaporization device by either, the annular collar being secured to the releasable securing means or the projection cooperatively interfitting within the receiving structure in the liquid vaporization device.

8. The liquid vaporization device as defined in claim 7 wherein the receiving structure is an opening.

9. The liquid vaporization device as defined in claim 7 wherein the releasable securing means comprises at least one latch that extends from the liquid vaporization device.

10. The liquid vaporization device as defined in claim 9 wherein the releasable securing means comprises a pair of latches that extend downwardly in the liquid vaporization device to grasp the annular collar.

11. A bottle adapted to be releasably interfitted with a plurality of liquid vaporization devices, each vaporization device having a housing differently dimensioned and adapted to receive a bottle containing a liquid to be vaporized, said bottle having at least two exterior surfaces and a neck forming an opening extending upwardly therefrom, the dimensions of said bottle and the location of said opening being predetermined such that the two predetermined exterior surfaces of said bottle are adapted to be located in different orientations with respect to each of the liquid vaporization devices to operatively interfit with each of the differently dimensioned housings.

12. A bottle as defined in claim 11 wherein said neck has an annular collar adapted to interfit with one of said plurality of liquid vaporization devices.

13. A bottle as defined in claim 11 wherein said bottle has first and second sets of opposed external surfaces, and said first set of opposed external surfaces each have at least one projection extending outwardly therefrom.

14. A bottle as defined in claim 13 wherein said opening in said bottle has a centerline and said centerline is located at about the midpoint between said first set of external opposed surfaces.

15. A bottle as defined in claim 14 wherein said centerline of said opening in said bottle is offset a predetermined distance away from the midpoint between said second set of opposed external opposed surfaces.

16. A bottle as defined in claim 15 wherein said neck has an annular collar adapted to interfit with one of said plurality of liquid vaporization devices.

17. A bottle for use with at least two differently dimensioned liquid vaporization devices, each of the vaporization devices having a heating chamber for receiving a wick containing a material to be vaporized, the bottle having a neck forming an opening, a set of opposed surfaces and a wick extending upwardly through the opening, the bottle being dimensioned to interfit to all of the at least two liquid vaporization devices to operatively locate the wick within the heating chamber of all of the at least two vaporization devices whereby the wick is heated by the liquid vaporization devices and wherein the bottle includes a fixation means to retain the bottle to all of the at least two liquid vaporization devices and wherein the fixation means includes both an annular collar surrounding the neck of the bottle and at least one projection extending outwardly from the set of opposed surfaces wherein the retaining of the bottle by either the annular collar or the at least one projection to all of the at least two liquid vaporization devices positions the wick of the bottle within the heating chamber of all of the at least two vaporization devices.

18. A bottle adapted to be releasably interfitted with at least two liquid vaporization devices, each vaporization device having a housing differently dimensioned and adapted to receive a bottle containing a liquid to be vaporized, one of the at least two vaporization devices having an opening and another vaporization device having a releasable securing means, the bottle having a neck forming an outlet opening extending therefrom, the bottle also having a projection extending outwardly therefrom and an annular collar surrounding the neck, the dimensions of the bottle and the location of the outlet opening being predetermined such that the bottle is adapted to operatively interfit with each of the differently dimensioned housings with either the projection interfitted through the opening in the housing or the annular collar interfitted to the releasable securing means.

19. A bottle adapted to be releasably interfitted with a first and a second liquid vaporization device, each of the first and second vaporization devices having a housing differently dimensioned and adapted to receive a bottle containing a liquid to be vaporized, each of the first and second liquid vaporization devices having a heater, the bottle having an upstanding neck and a wick having a first end located within the bottle and a second end extending upwardly through the neck, the first liquid vaporization device having a first affixation system wherein the bottle is dimensioned to fit into the housing to engage the housing to affix the bottle to the housing, the second liquid vaporization device having a second affixation means adapted to engage an annular collar formed on the upstanding neck of the bottle, the dimensions of the bottle and the location of the outlet opening being predetermined such that the bottle is adapted to operatively interfit with both the first and second liquid vaporization devices by utilizing the first affixation system or the second affixation system, but not both the first and second affixation systems, such that the second end of the wick is located so as to be heated by the heater to evaporate liquid.

20. A bottle adapted to be releasably interfitted with a first and a second liquid vaporization device, the first vaporization device having a housing having predetermined dimensions such that the bottle can be affixed to the housing by cooperatively fitting into the housing and the second vaporization device having a releasable securing means adapted to engage an annular collar formed on the bottle to affix the bottle to the second vaporization device.

21. A bottle adapted to be releasably interfitted with at least two different liquid vaporization devices, one of the liquid vaporization devices having an internal housing having predetermined dimensions such that the bottle can be affixed to the internal housing by cooperatively fitting into the internal housing and another vaporization device having a releasable securing means adapted to engage an annular collar formed on the bottle to affix the bottle thereto, wherein the bottle can be affixed to the one or the another liquid vaporization devices, respectively, by means of the interfitting of the bottle into the internal housing or the engagement of the releasable securing means with the annular collar.

22. A method of interfitting a bottle into any one of at least two different housings in liquid vaporization devices, one of the liquid vaporization devices having an opening and another having a releasable securing means, said method comprising the steps of:

providing a bottle having an outlet opening and two pairs of opposed external surfaces wherein the outlet opening is located at a midpoint between one of the pairs of opposed eternal surfaces and offset a predetermined distance from the midpoint between the other pair of opposed external surfaces, the bottle having an annular collar surrounding the outlet opening and a projection extending outwardly therefrom, inserting the bottle into one of the housings of the liquid vaporization devices to either interlock the projection into the opening or interlocking the collar into the releasable securing means to affix the bottle to a liquid vaporization device.

* * * * *